(12) United States Patent
Kirschman

(10) Patent No.: US 9,987,052 B2
(45) Date of Patent: Jun. 5, 2018

(54) MODULAR INTERSPINOUS FIXATION SYSTEM WITH THREADED COMPONENT

(71) Applicant: X-spine Systems, Inc., Miamisburg, OH (US)

(72) Inventor: David Louis Kirschman, Dayton, OH (US)

(73) Assignee: X-Spine Systems, Inc., Miamisburg, OH (US)

( * ) Notice: Subject to any disclaimer, the term of this patent is extended or adjusted under 35 U.S.C. 154(b) by 0 days. days.

(21) Appl. No.: 15/050,829

(22) Filed: Feb. 23, 2016

(65) Prior Publication Data

US 2016/0242824 A1    Aug. 25, 2016

Related U.S. Application Data

(60) Provisional application No. 62/120,091, filed on Feb. 24, 2015.

(51) Int. Cl.
*A61B 17/70* (2006.01)

(52) U.S. Cl.
CPC .................. *A61B 17/7068* (2013.01)

(58) Field of Classification Search
CPC .............. A61B 17/7061; A61B 17/842; A61B 17/7062; A61B 17/7068; A61B 17/7058; A61B 2050/311; A61B 2017/004776
USPC ........................................... 623/17.11–17.16
See application file for complete search history.

(56) References Cited

U.S. PATENT DOCUMENTS

| | | |
|---|---|---|
| 1,025,008 A | 4/1912 | Miner |
| 1,037,577 A | 9/1912 | Baker |
| 2,677,369 A | 5/1954 | Knowles |
| 3,426,364 A | 2/1969 | Lumb |
| 3,648,691 A | 3/1972 | Lumb et al. |
| 3,846,601 A | 11/1974 | Leeds |
| 3,867,728 A | 2/1975 | Stubstad et al. |
| 4,157,715 A | 6/1979 | Westerhoff |

(Continued)

FOREIGN PATENT DOCUMENTS

| | | |
|---|---|---|
| CA | 1292596 | 12/1991 |
| CA | 2133276 | 4/1995 |

(Continued)

OTHER PUBLICATIONS

"Materials Data Book," Cambridge University Engineering Department, 2003, 41 pages [retrieved from: www-mdp.eng.cam.ac.uk/web/library/enginfo/cueddatabooks/materials.pdf].

(Continued)

*Primary Examiner* — Pedro Philogene
(74) *Attorney, Agent, or Firm* — Sheridan Ross P.C.

(57) ABSTRACT

A modular interspinous system is shown having a first plate, a generally opposing second plate and a modular insert that may be removably or permanently secured to the first plate. The first plate has a coupling means, coupler or connection system in the form of a screw that may be permanently or non-permanently docked or supported in the first plate. The modular insert is adapted, sized and shaped to expose at least a portion of the screw thread of the screw and that portion may cooperate with at least one mating female thread in the second plate, thereby enabling a user to rotate the screw in order to drive the first and second plates towards or away from each other and, for example, into compression with bone.

20 Claims, 7 Drawing Sheets

(56) References Cited

U.S. PATENT DOCUMENTS

| | | |
|---|---|---|
| 4,194,384 A | 3/1980 | Fujie et al. |
| 4,257,409 A | 3/1981 | Bacal et al. |
| 4,309,777 A | 1/1982 | Patil |
| 4,349,921 A | 9/1982 | Kuntz |
| 4,401,112 A | 8/1983 | Rezaian |
| 4,488,543 A | 12/1984 | Tomier |
| 4,553,273 A | 11/1985 | Wu |
| 4,599,086 A | 7/1986 | Doty |
| 4,604,995 A | 8/1986 | Stephens et al. |
| 4,611,581 A | 9/1986 | Steffee |
| 4,611,582 A | 9/1986 | Duff |
| 4,657,550 A | 4/1987 | Daher |
| 4,696,290 A | 9/1987 | Steffee |
| 4,713,076 A | 12/1987 | Draenert |
| 4,714,469 A | 12/1987 | Kenna |
| 4,743,256 A | 5/1988 | Brantigan |
| 4,759,766 A | 7/1988 | Buettner-Janz et al. |
| 4,763,456 A | 8/1988 | Giannuzzi |
| 4,790,303 A | 12/1988 | Steffee |
| 4,827,918 A | 5/1989 | Olerud |
| 4,828,563 A | 5/1989 | Muller-Lierheim |
| 4,834,757 A | 5/1989 | Brantigan |
| 4,863,477 A | 9/1989 | Monson |
| 4,865,603 A | 9/1989 | Nioles |
| 4,878,915 A | 11/1989 | Brantigan |
| 4,904,261 A | 2/1990 | Dove et al. |
| 4,988,349 A | 1/1991 | Pennig |
| 4,997,432 A | 3/1991 | Keller |
| 5,041,113 A | 8/1991 | Biedermann et al. |
| 5,071,437 A | 12/1991 | Steffee |
| 5,084,049 A | 1/1992 | Asher et al. |
| 5,085,660 A | 2/1992 | Lin |
| 5,180,381 A | 1/1993 | Aust et al. |
| 5,192,327 A | 3/1993 | Brantigan |
| 5,246,443 A | 9/1993 | Mai |
| 5,261,911 A | 11/1993 | Carl |
| 5,267,423 A | 12/1993 | Giannuzzi |
| 5,275,601 A | 1/1994 | Gogolewski et al. |
| 5,290,312 A | 3/1994 | Kojimoto et al. |
| 5,306,307 A | 4/1994 | Senter et al. |
| 5,306,308 A | 4/1994 | Gross et al. |
| 5,324,290 A | 6/1994 | Zdeblick et al. |
| 5,330,473 A | 7/1994 | Howland |
| 5,364,399 A | 11/1994 | Lowery et al. |
| 5,366,455 A | 11/1994 | Dove et al. |
| 5,405,391 A | 4/1995 | Henderson et al. |
| 5,425,772 A | 6/1995 | Brantigan |
| 5,439,463 A | 8/1995 | Lin |
| 5,443,514 A | 8/1995 | Steffee |
| 5,454,812 A | 10/1995 | Lin |
| 5,496,318 A | 3/1996 | Howland et al. |
| 5,505,736 A | 4/1996 | Reimels et al. |
| 5,507,815 A | 4/1996 | Wagner et al. |
| 5,522,899 A | 6/1996 | Michelson |
| 5,534,030 A | 7/1996 | Navarro et al. |
| 5,549,612 A | 8/1996 | Yapp et al. |
| 5,554,191 A | 9/1996 | Lahille et al. |
| 5,601,551 A | 2/1997 | Taylor et al. |
| 5,601,553 A | 2/1997 | Trebing et al. |
| 5,607,607 A | 3/1997 | Naiman et al. |
| 5,609,635 A | 3/1997 | Michelson |
| 5,609,636 A | 3/1997 | Kohrs et al. |
| 5,609,637 A | 3/1997 | Biedermann et al. |
| 5,616,142 A | 4/1997 | Yuan et al. |
| 5,616,144 A | 4/1997 | Yapp et al. |
| 5,620,443 A | 4/1997 | Gertzbein et al. |
| 5,645,599 A | 7/1997 | Samani |
| 5,672,175 A | 9/1997 | Martin |
| 5,672,177 A | 9/1997 | Seldin |
| 5,681,310 A | 10/1997 | Yuan et al. |
| 5,681,311 A | 10/1997 | Foley et al. |
| 5,683,463 A | 11/1997 | Godefroy et al. |
| 5,702,395 A | 12/1997 | Hopf |
| 5,702,450 A | 12/1997 | Bisserie |
| 5,702,452 A | 12/1997 | Argenson et al. |
| 5,702,453 A | 12/1997 | Rabbe et al. |
| 5,713,899 A | 2/1998 | Marney et al. |
| 5,713,900 A | 2/1998 | Benzel et al. |
| 5,716,415 A | 2/1998 | Steffee |
| 5,720,746 A | 2/1998 | Soubeiran |
| 5,747,106 A | 5/1998 | Matsunaga |
| 5,776,196 A | 7/1998 | Matsuzaki et al. |
| 5,800,548 A | 9/1998 | Martin et al. |
| 5,824,094 A | 10/1998 | Serhan et al. |
| 5,836,948 A | 11/1998 | Zucherman et al. |
| 5,843,082 A | 12/1998 | Yuan et al. |
| 5,860,977 A | 1/1999 | Zucherman et al. |
| 5,865,845 A | 2/1999 | Thalgott |
| 5,876,402 A | 3/1999 | Errico et al. |
| 5,876,404 A | 3/1999 | Zucherman et al. |
| 5,876,457 A | 3/1999 | Picha et al. |
| 5,888,228 A | 3/1999 | Knothe et al. |
| 5,904,683 A | 5/1999 | Pohndorf et al. |
| 5,925,047 A | 7/1999 | Errico et al. |
| 5,951,558 A | 9/1999 | Fiz |
| 5,954,722 A | 9/1999 | Bono |
| 5,980,522 A | 11/1999 | Koros et al. |
| 6,008,432 A | 12/1999 | Taylor |
| 6,030,389 A | 2/2000 | Wagner et al. |
| 6,048,342 A | 4/2000 | Zucherman et al. |
| 6,066,175 A | 5/2000 | Henderson et al. |
| 6,068,630 A | 5/2000 | Zucherman et al. |
| 6,090,112 A | 7/2000 | Zucherman et al. |
| 6,106,557 A | 8/2000 | Robioneck et al. |
| 6,132,464 A | 10/2000 | Martin |
| 6,136,002 A | 10/2000 | Shih et al. |
| 6,139,550 A | 10/2000 | Michelson |
| 6,139,579 A | 10/2000 | Steffee et al. |
| 6,143,033 A | 11/2000 | Paul et al. |
| 6,152,926 A | 11/2000 | Zucherman et al. |
| 6,152,927 A | 11/2000 | Farris et al. |
| 6,156,038 A | 12/2000 | Zucherman et al. |
| 6,158,437 A | 12/2000 | Vagley |
| 6,159,211 A | 12/2000 | Boriani et al. |
| 6,159,213 A | 12/2000 | Rogozinski |
| 6,159,245 A | 12/2000 | Meriwether et al. |
| 6,171,307 B1 | 1/2001 | Orlich |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,193,721 B1 | 2/2001 | Michelson |
| D440,311 S | 4/2001 | Michelson |
| 6,224,602 B1 | 5/2001 | Hayes |
| 6,235,030 B1 | 5/2001 | Zucherman et al. |
| 6,235,033 B1 | 5/2001 | Brace et al. |
| 6,235,034 B1 | 5/2001 | Bray |
| 6,235,059 B1 | 5/2001 | Benezech et al. |
| 6,238,397 B1 | 5/2001 | Zucherman et al. |
| 6,241,771 B1 | 6/2001 | Gresser et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,655 B1 | 7/2001 | Psharodi |
| 6,293,949 B1 | 9/2001 | Justis et al. |
| D449,692 S | 10/2001 | Michelson |
| 6,306,136 B1 | 10/2001 | Baccelli |
| 6,306,139 B1 | 10/2001 | Fuentes |
| 6,328,738 B1 | 12/2001 | Suddaby |
| 6,332,882 B1 | 12/2001 | Zucherman et al. |
| 6,332,883 B1 | 12/2001 | Zucherman et al. |
| 6,346,122 B1 | 2/2002 | Picha et al. |
| 6,358,254 B1 | 3/2002 | Anderson |
| 6,361,537 B1 | 3/2002 | Anderson |
| 6,364,883 B1 | 4/2002 | Santilli |
| 6,368,351 B1 | 4/2002 | Glenn et al. |
| 6,371,986 B1 | 4/2002 | Bagby |
| 6,379,355 B1 | 4/2002 | Zucherman et al. |
| 6,383,186 B1 | 5/2002 | Michelson |
| 6,398,783 B1 | 6/2002 | Michelson |
| 6,413,259 B1 | 7/2002 | Lyons et al. |
| 6,416,528 B1 | 7/2002 | Michelson |
| 6,419,676 B1 | 7/2002 | Zucherman et al. |

(56) References Cited

U.S. PATENT DOCUMENTS

| | | |
|---|---|---|
| 6,419,677 B2 | 7/2002 | Zucherman et al. |
| 6,428,542 B1 | 8/2002 | Michelson |
| 6,432,106 B1 | 8/2002 | Frser |
| 6,432,107 B1 | 8/2002 | Ferree |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,454,769 B2 | 9/2002 | Wagner et al. |
| 6,454,771 B1 | 9/2002 | Michelson |
| 6,454,806 B1 | 9/2002 | Cohen et al. |
| 6,454,807 B1 | 9/2002 | Jackson |
| 6,458,159 B1 | 10/2002 | Thalgott |
| 6,478,796 B2 | 11/2002 | Zucherman et al. |
| 6,485,517 B1 | 11/2002 | Michelson |
| 6,491,723 B1 | 12/2002 | Beaty |
| 6,500,178 B2 | 12/2002 | Zucherman et al. |
| 6,503,250 B2 | 1/2003 | Pul |
| 6,652,527 B2 | 1/2003 | Zucherman et al. |
| 6,514,256 B2 | 2/2003 | Zucherman et al. |
| 6,520,993 B2 | 2/2003 | James et al. |
| 6,527,776 B1 | 3/2003 | Michelson |
| 6,528,089 B1 | 3/2003 | Kothrade et al. |
| 6,533,786 B1 | 3/2003 | Needham et al. |
| 6,558,423 B1 | 5/2003 | Michelson |
| 6,558,424 B2 | 5/2003 | Thalgott |
| 6,562,074 B2 | 5/2003 | Gerbec et al. |
| 6,569,201 B2 | 5/2003 | Moumene et al. |
| 6,572,619 B2 | 6/2003 | Santilli |
| 6,572,654 B1 | 6/2003 | Santilli |
| 6,575,975 B2 | 6/2003 | Brace et al. |
| 6,579,319 B2 | 6/2003 | Goble et al. |
| 6,582,432 B1 | 6/2003 | Michelson |
| 6,582,433 B2 | 6/2003 | Yun |
| 6,592,586 B1 | 7/2003 | Michelson |
| 6,592,624 B1 | 7/2003 | Fraser et al. |
| 6,599,290 B2 | 7/2003 | Bailey et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,620,196 B1 | 9/2003 | Trieu |
| 6,626,907 B2 | 9/2003 | Campbell et al. |
| 6,626,944 B1 | 9/2003 | Taylor |
| 6,641,585 B2 | 11/2003 | Sato et al. |
| 6,641,586 B2 | 11/2003 | Sato et al. |
| 6,652,525 B1 | 11/2003 | Assaker et al. |
| 6,652,534 B2 | 11/2003 | Zucherman et al. |
| 6,669,700 B1 | 12/2003 | Farris et al. |
| 6,669,732 B2 | 12/2003 | Serhan et al. |
| 6,676,703 B2 | 1/2004 | Biscup |
| 6,679,883 B2 | 1/2004 | Hawkes et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,699,249 B2 | 3/2004 | Schlapfer et al. |
| 6,712,818 B1 | 3/2004 | Michelson |
| 6,712,819 B2 | 3/2004 | Zucherman et al. |
| 6,719,794 B2 | 4/2004 | Gerber et al. |
| 6,730,127 B2 | 5/2004 | Michelson |
| 6,755,833 B1 | 6/2004 | Paul et al. |
| 6,761,720 B1 | 7/2004 | Senegas |
| 6,776,781 B1 | 8/2004 | Uwaydah |
| 6,776,798 B2 | 8/2004 | Camino et al. |
| 6,835,206 B2 | 12/2004 | Jackson |
| 6,837,905 B1 | 1/2005 | Lieberman |
| 6,852,113 B2 | 2/2005 | Nathanson et al. |
| 6,852,129 B2 | 2/2005 | Gerbec et al. |
| 6,863,673 B2 | 3/2005 | Gerbec et al. |
| 6,890,334 B2 | 5/2005 | Brace et al. |
| 6,916,320 B2 | 7/2005 | Michelson |
| 6,921,264 B2 | 7/2005 | Mayer et al. |
| 6,926,737 B2 | 8/2005 | Jackson |
| 6,936,050 B2 | 8/2005 | Michelson |
| 6,936,051 B2 | 8/2005 | Michelson |
| 6,946,000 B2 | 9/2005 | Senegas et al. |
| 6,964,664 B2 | 11/2005 | Field et al. |
| 6,964,883 B2 | 11/2005 | Chang |
| 6,969,390 B2 | 11/2005 | Michelson |
| 6,974,479 B2 | 12/2005 | Trieu |
| 7,001,387 B2 | 2/2006 | Farris et al. |
| 7,008,226 B2 | 3/2006 | Mayer et al. |
| 7,018,414 B2 | 3/2006 | Brau |
| 7,029,473 B2 | 4/2006 | Zucherman et al. |
| 7,033,394 B2 | 4/2006 | Michelson |
| 7,041,105 B2 | 5/2006 | Michelson |
| 7,041,135 B2 | 5/2006 | Michelson |
| 7,044,952 B2 | 5/2006 | Michelson |
| 7,048,736 B2 | 5/2006 | Robinson et al. |
| 7,048,739 B2 | 5/2006 | Konieczynski et al. |
| 7,060,097 B2 | 6/2006 | Fraser et al. |
| 7,074,221 B2 | 7/2006 | Michelson |
| 7,077,843 B2 | 7/2006 | Thramann et al. |
| 7,087,083 B2 | 8/2006 | Pasquet et al. |
| 7,097,645 B2 | 8/2006 | Michelson |
| 7,112,202 B2 | 9/2006 | Michelson |
| 7,112,222 B2 | 9/2006 | Fraser et al. |
| 7,115,130 B2 | 10/2006 | Michelson |
| 7,118,573 B2 | 10/2006 | Michelson |
| 7,137,984 B2 | 11/2006 | Michelson |
| 7,163,561 B2 | 1/2007 | Michelson |
| 7,182,782 B2 | 2/2007 | Kirschman |
| 7,186,256 B2 | 3/2007 | Michelson |
| 7,201,751 B2 * | 4/2007 | Zucherman ............ A61K 31/37 606/249 |
| 7,201,753 B2 | 4/2007 | Schlapfer et al. |
| 7,217,293 B2 | 5/2007 | Branch, Jr. |
| 7,226,483 B2 | 6/2007 | Gerber et al. |
| 7,229,477 B2 | 6/2007 | Biscup |
| 7,232,463 B2 | 6/2007 | Falahee |
| 7,238,203 B2 | 7/2007 | Bagga et al. |
| 7,255,699 B2 | 8/2007 | Paul |
| 7,273,481 B2 | 9/2007 | Lombardo et al. |
| 7,276,081 B1 | 10/2007 | Coates et al. |
| 7,276,082 B2 | 10/2007 | Zdeblick et al. |
| 7,303,564 B2 | 12/2007 | Freid et al. |
| 7,306,628 B2 | 12/2007 | Zucherman et al. |
| 7,311,712 B2 | 12/2007 | Dalton |
| 7,320,707 B2 | 1/2008 | Zucherman et al. |
| 7,335,203 B2 | 2/2008 | Winslow et al. |
| 7,399,301 B2 | 7/2008 | Michelson |
| 7,445,627 B2 | 11/2008 | Hawkes et al. |
| 7,503,933 B2 | 3/2009 | Michelson |
| 7,510,567 B2 | 3/2009 | Zucherman et al. |
| 7,537,603 B2 | 5/2009 | Huebner et al. |
| 7,549,999 B2 | 6/2009 | Zucherman et al. |
| 7,556,648 B2 | 7/2009 | Picha et al. |
| 7,585,313 B2 | 9/2009 | Kwak et al. |
| 7,585,316 B2 | 9/2009 | Trieu |
| 7,588,591 B2 | 9/2009 | Hartmann et al. |
| 7,588,592 B2 | 9/2009 | Winslow et al. |
| 7,594,931 B2 | 9/2009 | Louis et al. |
| 7,611,527 B2 | 11/2009 | Freid et al. |
| 7,621,939 B2 | 11/2009 | Zucherman et al. |
| 7,621,956 B2 | 11/2009 | Paul et al. |
| 7,628,816 B2 | 12/2009 | Magerl et al. |
| 7,635,377 B2 | 12/2009 | Zucherman et al. |
| 7,637,950 B2 | 12/2009 | Baccelli et al. |
| 7,637,951 B2 | 12/2009 | Michelson |
| 7,637,953 B2 | 12/2009 | Branch et al. |
| 7,637,954 B2 | 12/2009 | Michelson |
| 7,641,666 B2 | 1/2010 | Paul et al. |
| 7,641,701 B2 | 1/2010 | Kirschman |
| 7,651,517 B2 | 1/2010 | Konieczynski et al. |
| 7,655,028 B2 | 2/2010 | Kirschman |
| 7,655,046 B2 | 2/2010 | Dryer et al. |
| 7,658,752 B2 | 2/2010 | Labrom et al. |
| 7,662,154 B2 | 2/2010 | Ribeiro |
| 7,666,208 B1 | 2/2010 | Asfora |
| 7,670,380 B2 | 3/2010 | Cauthen, III |
| 7,678,148 B2 | 3/2010 | Peterman |
| 7,691,130 B2 | 4/2010 | Bruneau et al. |
| 7,695,496 B2 | 4/2010 | Labrom et al. |

(56) References Cited

U.S. PATENT DOCUMENTS

| | | |
|---|---|---|
| 7,699,880 B2 | 4/2010 | Orbay et al. |
| 7,704,280 B2 | 4/2010 | Lechmann et al. |
| 7,723,395 B2 | 5/2010 | Ringeisen et al. |
| 7,727,233 B2 | 6/2010 | Blackwell et al. |
| 7,763,051 B2 | 7/2010 | Labrom et al. |
| 7,763,073 B2 | 7/2010 | Hawkins et al. |
| 7,776,091 B2 | 8/2010 | Mastroirio et al. |
| 7,780,708 B2 | 8/2010 | Morris et al. |
| 7,846,190 B2 | 12/2010 | Ball |
| 7,857,987 B2 | 12/2010 | Beaty |
| 7,871,426 B2 | 1/2011 | Chin et al. |
| 7,892,262 B2 | 2/2011 | Rhoda et al. |
| 7,909,853 B2 | 3/2011 | Zucherman et al. |
| 7,931,674 B2 | 4/2011 | Zucherman et al. |
| 7,938,860 B2 | 5/2011 | Trieu |
| 7,955,362 B2 | 6/2011 | Erickson et al. |
| 7,963,982 B2 | 6/2011 | Kirschman |
| 7,988,733 B2 | 8/2011 | Shimp et al. |
| 7,988,734 B2 | 8/2011 | Peterman et al. |
| 8,002,837 B2 | 8/2011 | Stream et al. |
| 8,029,542 B2 | 10/2011 | Zucherman et al. |
| 8,034,084 B2 | 10/2011 | Landry et al. |
| 8,043,377 B2 | 10/2011 | Guyer et al. |
| 8,062,367 B2 | 11/2011 | Kirschman |
| 8,088,163 B1 | 1/2012 | Kleiner |
| 8,097,019 B2 | 1/2012 | Mitchell et al. |
| 8,097,036 B2 | 1/2012 | Cordaro et al. |
| 8,182,532 B2 | 5/2012 | Anderson et al. |
| 8,182,539 B2 | 5/2012 | Tyber et al. |
| 8,226,653 B2 | 7/2012 | Blackwell et al. |
| 8,252,059 B2 | 8/2012 | Overes et al. |
| 8,262,697 B2 | 9/2012 | Kirschman |
| 8,262,737 B2 | 9/2012 | Bagga et al. |
| 8,268,002 B2 | 9/2012 | Blackwell et al. |
| 8,282,682 B2 | 10/2012 | Kirschman |
| 8,343,190 B1 | 1/2013 | Mueller et al. |
| 8,343,219 B2 | 1/2013 | Allain et al. |
| 8,343,223 B2 | 1/2013 | Bucci |
| 8,372,152 B2 | 2/2013 | Kirschman |
| 8,470,038 B2 | 6/2013 | Bianchi et al. |
| 8,535,356 B2 | 9/2013 | Kirschman |
| 8,585,764 B2 | 11/2013 | Copf, Jr. |
| 8,663,293 B2 | 3/2014 | Assell et al. |
| 8,728,130 B2 | 5/2014 | Kirschman |
| 8,734,493 B2 | 5/2014 | Kirschman |
| 8,795,370 B2 | 8/2014 | Kirschman |
| 8,821,553 B2 | 9/2014 | Kirschman |
| 8,932,333 B2 | 1/2015 | Kirschman |
| 8,979,934 B2 | 3/2015 | Kirschman |
| 9,078,706 B2 | 7/2015 | Kirschman |
| 9,439,689 B2 | 9/2016 | Kirschman |
| 9,486,263 B2 | 11/2016 | Kirschman |
| 2001/0016773 A1 | 8/2001 | Serhan et al. |
| 2001/0039454 A1 | 11/2001 | Ricci et al. |
| 2002/0004683 A1 | 1/2002 | Michelson |
| 2002/0022888 A1 | 2/2002 | Serhan et al. |
| 2002/0029039 A1 | 3/2002 | Zucherman et al. |
| 2002/0045898 A1 | 4/2002 | Freid et al. |
| 2002/0058939 A1 | 5/2002 | Wagner et al. |
| 2002/0065557 A1 | 5/2002 | Goble et al. |
| 2002/0091446 A1 | 7/2002 | Zucherman et al. |
| 2002/0120273 A1 | 8/2002 | Needham et al. |
| 2002/0133232 A1 | 9/2002 | Ricci et al. |
| 2002/0138146 A1 | 9/2002 | Jackson |
| 2002/0143331 A1 | 10/2002 | Zucherman et al. |
| 2002/0143400 A1 | 10/2002 | Biscup |
| 2002/0173790 A1 | 11/2002 | Chang et al. |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023307 A1 | 1/2003 | Michelson |
| 2003/0040746 A1 | 2/2003 | Mitchell et al. |
| 2003/0045880 A1 | 3/2003 | Michelson |
| 2003/0060828 A1 | 3/2003 | Michelson |
| 2003/0065393 A1 | 4/2003 | Moumene |
| 2003/0078668 A1 | 4/2003 | Michelson |
| 2003/0093082 A1 | 5/2003 | Campbell et al. |
| 2003/0100951 A1 | 5/2003 | Serhan et al. |
| 2003/0105462 A1 | 6/2003 | Haider |
| 2003/0120274 A1 | 6/2003 | Morris et al. |
| 2003/0139812 A1 | 7/2003 | Garcia et al. |
| 2003/0181912 A1 | 9/2003 | Michelson |
| 2003/0187443 A1 | 10/2003 | Lauryssen et al. |
| 2003/0191471 A1 | 10/2003 | Michelson |
| 2003/0191472 A1 | 10/2003 | Michelson |
| 2003/0199876 A1 | 10/2003 | Brace et al. |
| 2003/0199983 A1 | 10/2003 | Michelson |
| 2003/0208204 A1 | 11/2003 | Bailey et al. |
| 2003/0225409 A1 | 12/2003 | Freid et al. |
| 2004/0019353 A1 | 1/2004 | Freid et al. |
| 2004/0030338 A1 | 2/2004 | Paul et al. |
| 2004/0033180 A1 | 2/2004 | Mayer et al. |
| 2004/0053196 A1 | 3/2004 | Mayer et al. |
| 2004/0092939 A1 | 5/2004 | Freid et al. |
| 2004/0097934 A1 | 5/2004 | Farris et al. |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127901 A1 | 7/2004 | Huebner et al. |
| 2004/0127903 A1 | 7/2004 | Schlapfer et al. |
| 2004/0127904 A1 | 7/2004 | Konieczynski et al. |
| 2004/0133205 A1 | 7/2004 | Thramann et al. |
| 2004/0181226 A1 | 9/2004 | Michelson |
| 2004/0181229 A1 | 9/2004 | Michelson |
| 2004/0181286 A1 | 9/2004 | Michelson |
| 2004/0186476 A1 | 9/2004 | Michelson |
| 2004/0193269 A1 | 9/2004 | Fraser et al. |
| 2004/0193270 A1 | 9/2004 | DiMauro et al. |
| 2004/0193271 A1 | 9/2004 | Fraser et al. |
| 2004/0199254 A1 | 10/2004 | Louis et al. |
| 2004/0210313 A1 | 10/2004 | Michelson |
| 2004/0210314 A1 | 10/2004 | Michelson |
| 2004/0230309 A1 | 11/2004 | DiMauro et al. |
| 2005/0038511 A1 | 2/2005 | Martz et al. |
| 2005/0038513 A1 | 2/2005 | Michelson |
| 2005/0043800 A1 | 2/2005 | Paul et al. |
| 2005/0096657 A1 | 5/2005 | Autericque et al. |
| 2005/0119758 A1 | 6/2005 | Alexander et al. |
| 2005/0187551 A1 | 8/2005 | Orbay et al. |
| 2005/0192576 A1 | 9/2005 | Michelson |
| 2005/0203512 A1 | 9/2005 | Hawkins et al. |
| 2005/0240182 A1 | 10/2005 | Zucherman et al. |
| 2005/0251137 A1 | 11/2005 | Ball |
| 2006/0004447 A1 | 1/2006 | Mastrorio et al. |
| 2006/0015181 A1 | 1/2006 | Elberg |
| 2006/0036325 A1 | 2/2006 | Paul et al. |
| 2006/0064166 A1 | 3/2006 | Zucherman et al. |
| 2006/0069440 A1 | 3/2006 | Zucherman et al. |
| 2006/0106381 A1 | 5/2006 | Ferree et al. |
| 2006/0129240 A1 | 6/2006 | Lessar et al. |
| 2006/0142761 A1 | 6/2006 | Landry et al. |
| 2006/0149376 A1 | 7/2006 | Shimp et al. |
| 2006/0217807 A1 | 9/2006 | Peterman et al. |
| 2006/0235533 A1 | 10/2006 | Blain |
| 2006/0241616 A1 | 10/2006 | Konieczynski et al. |
| 2006/0247634 A1 | 11/2006 | Warner et al. |
| 2006/0247640 A1* | 11/2006 | Blackwell ......... A61B 17/7068 606/71 |
| 2006/0264938 A1 | 11/2006 | Zucherman et al. |
| 2006/0276792 A1 | 12/2006 | Ensign |
| 2006/0282079 A1 | 12/2006 | Labrom et al. |
| 2007/0010826 A1 | 1/2007 | Rhoda et al. |
| 2007/0027544 A1 | 2/2007 | McCord et al. |
| 2007/0043366 A1 | 2/2007 | Pfefferle et al. |
| 2007/0055246 A1 | 3/2007 | Zucherman et al. |
| 2007/0073297 A1 | 3/2007 | Reynolds |
| 2007/0106388 A1 | 5/2007 | Michelson |
| 2007/0118125 A1 | 5/2007 | Orbay et al. |
| 2007/0162013 A1 | 7/2007 | Jacene et al. |
| 2007/0233082 A1 | 10/2007 | Chin et al. |
| 2007/0270840 A1 | 11/2007 | Chin et al. |
| 2007/0276499 A1 | 11/2007 | Paul et al. |

(56) References Cited

U.S. PATENT DOCUMENTS

| | | |
|---|---|---|
| 2008/0097444 A1 | 4/2008 | Erickson et al. |
| 2008/0114455 A1* | 5/2008 | Lange ............... A61B 17/7062 623/17.16 |
| 2008/0154377 A1 | 6/2008 | Voellmicke |
| 2008/0154378 A1 | 6/2008 | Pelo |
| 2008/0177306 A1 | 7/2008 | Lamborne et al. |
| 2008/0177391 A1 | 7/2008 | Mitchell et al. |
| 2008/0183210 A1 | 7/2008 | Zucherman et al. |
| 2008/0183211 A1 | 7/2008 | Lamborne et al. |
| 2008/0183293 A1 | 7/2008 | Parry et al. |
| 2008/0243193 A1 | 10/2008 | Ensign |
| 2009/0036985 A1 | 2/2009 | Whiting |
| 2009/0054986 A1 | 2/2009 | Cordaro et al. |
| 2009/0062862 A1 | 3/2009 | Perrow et al. |
| 2009/0082849 A1 | 3/2009 | Link |
| 2009/0234359 A1 | 9/2009 | Onoue et al. |
| 2009/0234458 A1 | 9/2009 | de Villiers et al. |
| 2009/0276051 A1 | 11/2009 | Arramon et al. |
| 2010/0042162 A1 | 2/2010 | Edie et al. |
| 2010/0042218 A1 | 2/2010 | Nebosky et al. |
| 2010/0070037 A1 | 3/2010 | Parry et al. |
| 2010/0087860 A1 | 4/2010 | Chin et al. |
| 2010/0087869 A1 | 4/2010 | Abdou |
| 2010/0106249 A1 | 4/2010 | Tyber et al. |
| 2010/0131074 A1 | 5/2010 | Shikinami |
| 2010/0211101 A1 | 8/2010 | Blackwell et al. |
| 2010/0262244 A1 | 10/2010 | Savage-Erickson et al. |
| 2010/0312347 A1 | 12/2010 | Arramon et al. |
| 2011/0015745 A1 | 1/2011 | Bucci |
| 2011/0022181 A1 | 1/2011 | Kasahara et al. |
| 2011/0040382 A1 | 2/2011 | Muhanna |
| 2011/0054531 A1 | 3/2011 | Lamborne et al. |
| 2011/0066186 A1* | 3/2011 | Boyer, II ........... A61B 17/7065 606/249 |
| 2011/0098745 A1 | 4/2011 | Liu et al. |
| 2011/0144692 A1* | 6/2011 | Saladin ............. A61B 17/7053 606/249 |
| 2011/0160776 A1 | 6/2011 | Erickson et al. |
| 2012/0006363 A1 | 1/2012 | Milojevic et al. |
| 2012/0022653 A1 | 1/2012 | Kirschman |
| 2012/0089184 A1* | 4/2012 | Yeh .................... A61B 17/7068 606/248 |
| 2012/0101579 A1 | 4/2012 | de Villiers et al. |
| 2012/0109302 A1 | 5/2012 | Miller et al. |
| 2012/0265306 A1 | 10/2012 | Trieu |
| 2012/0316650 A1 | 12/2012 | Ullrich et al. |
| 2013/0006363 A1 | 1/2013 | Ullrich, Jr. |
| 2013/0006367 A1 | 1/2013 | Bucci |
| 2013/0018471 A1 | 1/2013 | Davenport et al. |
| 2013/0116793 A1 | 5/2013 | Kloss |
| 2013/0131685 A1 | 5/2013 | Perrow |
| 2013/0197645 A1 | 8/2013 | Assell et al. |
| 2014/0200614 A1* | 7/2014 | Mitchell ............. A61B 17/1606 606/248 |
| 2014/0324173 A1 | 10/2014 | Kirschman |
| 2015/0157465 A1 | 6/2015 | Kirschman |
| 2016/0000576 A1 | 1/2016 | Kirschman |

FOREIGN PATENT DOCUMENTS

| | | |
|---|---|---|
| CA | 2163243 | 9/1995 |
| CA | 2383634 | 8/2001 |
| DE | 1139331 | 11/1962 |
| DE | 4409833 | 10/1995 |
| DE | 10101267 | 7/2002 |
| EP | 0179695 | 4/1986 |
| EP | 0307241 | 12/1992 |
| EP | 599640 | 6/1994 |
| EP | 1103237 | 5/2001 |
| EP | 1169971 | 1/2002 |
| EP | 1437105 | 7/2004 |
| EP | 1561429 | 8/2005 |
| FR | 2727005 | 5/1996 |
| FR | 2827150 | 1/2003 |
| FR | 2856272 | 12/2004 |
| WO | WO 89/09035 | 10/1989 |
| WO | WO 97/20526 | 6/1997 |
| WO | WO 99/63914 | 12/1999 |
| WO | WO 00/66044 | 11/2000 |
| WO | WO 00/66045 | 11/2000 |
| WO | WO 02/03885 | 1/2002 |
| WO | WO 2003/005939 | 1/2003 |
| WO | WO 2004/017857 | 3/2004 |
| WO | WO 2004/086990 | 10/2004 |
| WO | WO 2005/070346 | 8/2005 |
| WO | WO 2006/119092 | 11/2006 |
| WO | WO 2007/035582 | 3/2007 |
| WO | WO 2008/021656 | 2/2008 |
| WO | WO 2008/052971 | 5/2008 |
| WO | WO 2008/065443 | 6/2008 |
| WO | WO 2011/008864 | 1/2011 |

OTHER PUBLICATIONS

International Search Report and Written Opinion for International (PCT) Patent Application No. PCT/US2014/051821, dated Jan. 29, 2015 13 pages.

International Preliminary Report on Patentability for International (PCT) Patent Application No. PCT/US2014/051821, dated Mar. 24, 2016 9 pages.

International Search Report and Written Opinion for International (PCT) Patent Application No. PCT/US2010/058285, dated Jun. 5, 2011 22 pages.

International Preliminary Report on Patentability for International (PCT) Patent Application No. PCT/US2010/058285, dated Jul. 26, 2012 17 pages.

Official Action for European Patent Application No. 10787228.5, dated Mar. 24, 2015 3 pages.

Official Action for European Patent Application No. 10787228.5, dated Oct. 1, 2015 3 pages.

International Search Report and Written Opinion for International (PCT) Patent Application No. PCT/US2016/019115, dated Jul. 12, 2016 14 pages.

* cited by examiner

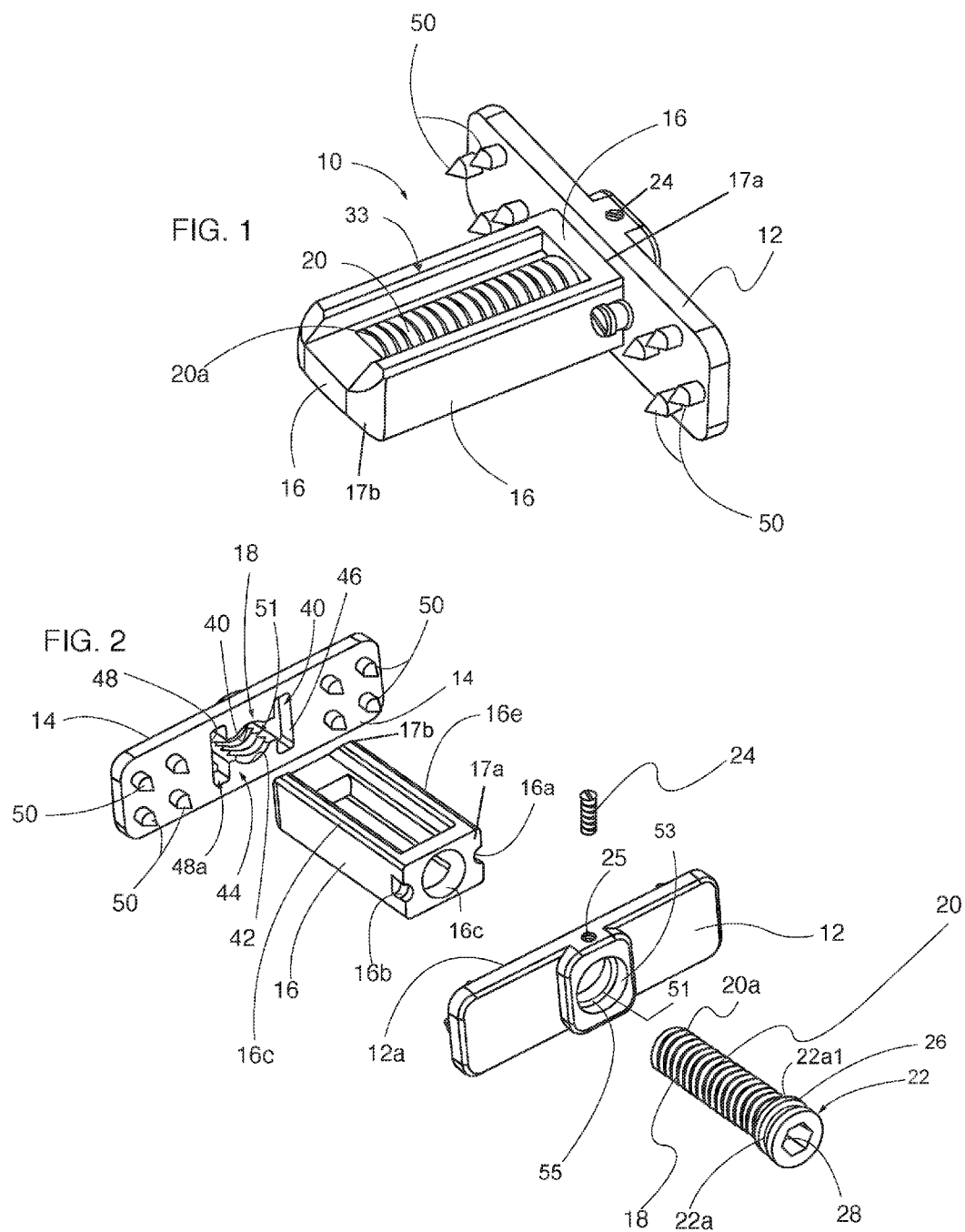

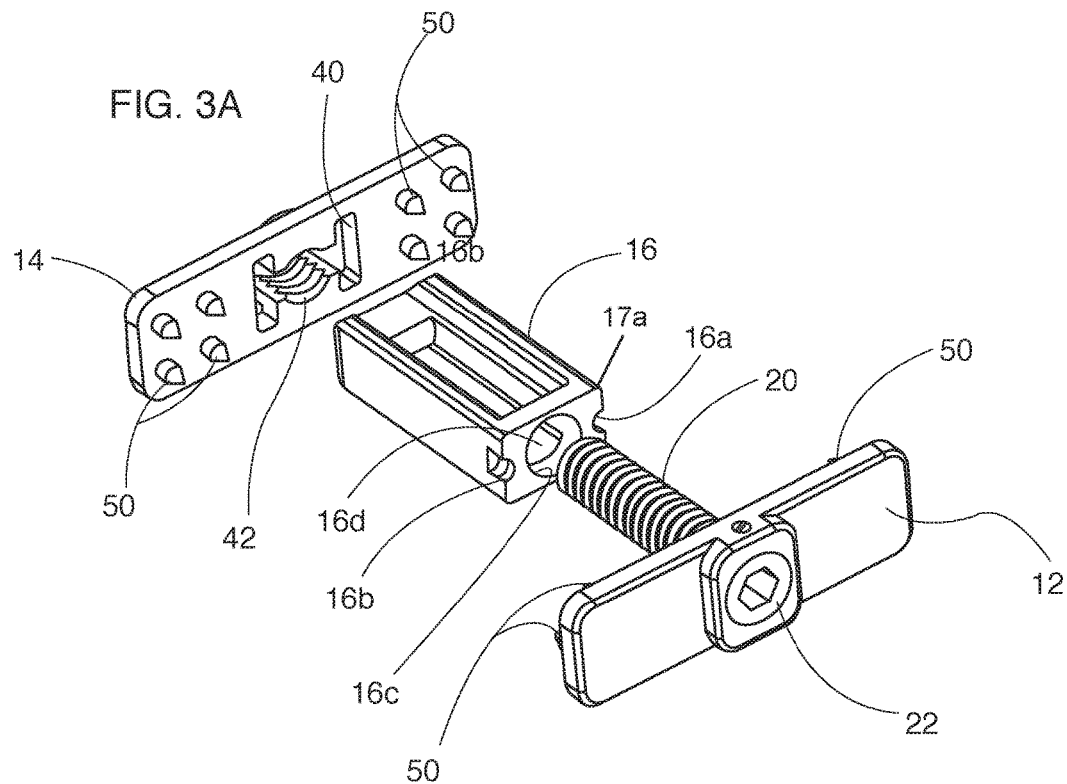
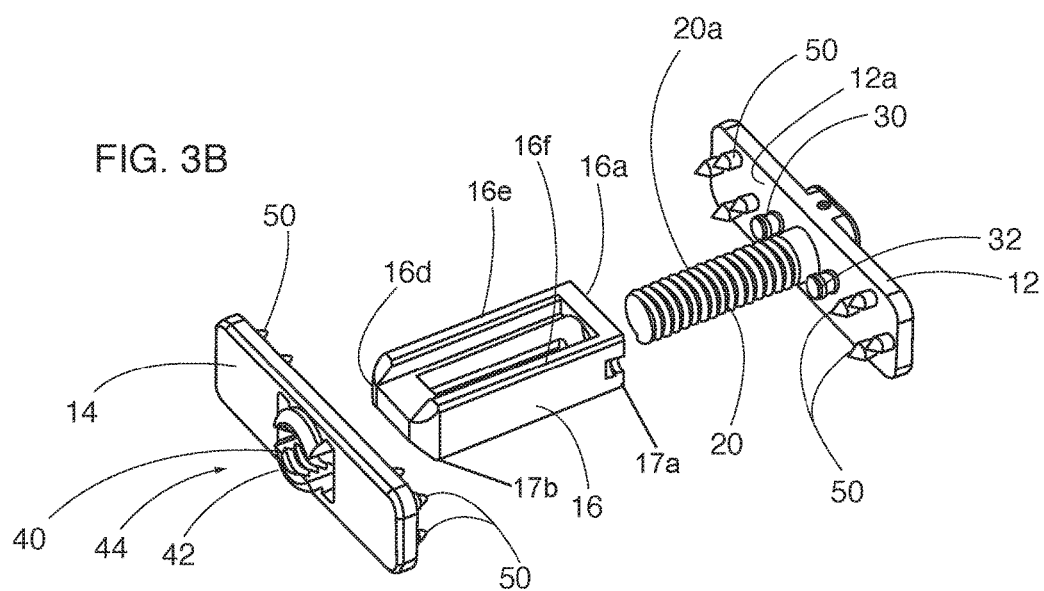

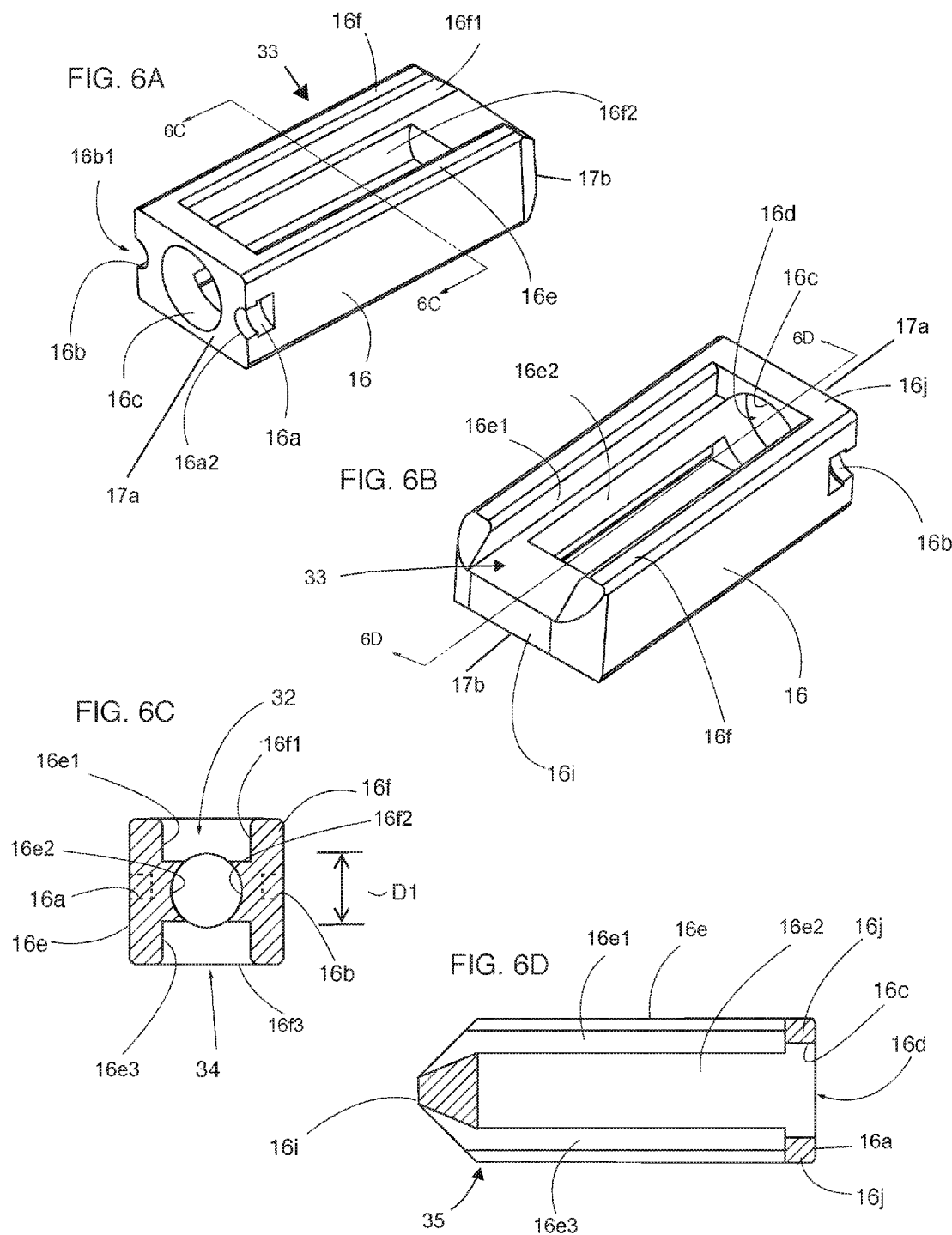

FIG 7
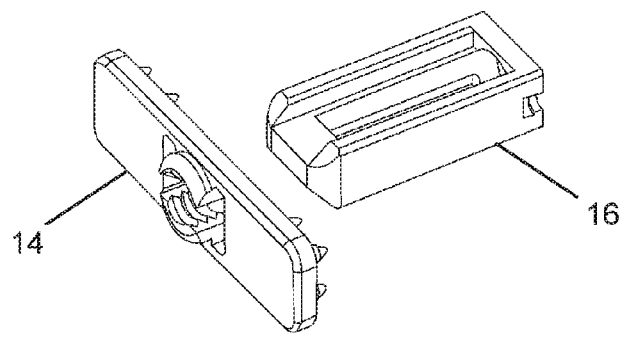
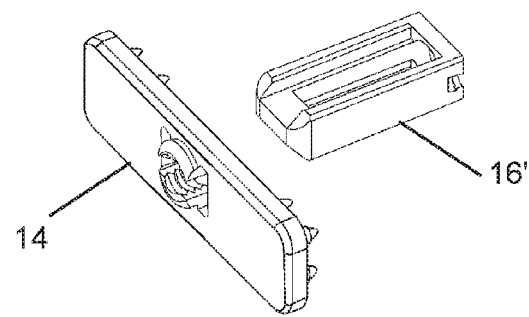
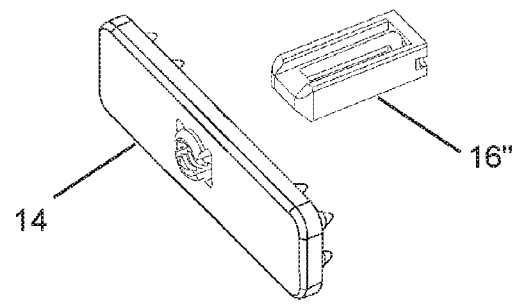
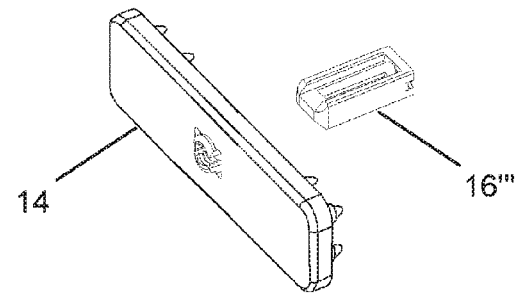

MODULAR INTERSPINOUS FIXATION SYSTEM WITH THREADED COMPONENT

CROSS-REFERENCE TO RELATED APPLICATION

The present application claims priority to provisional U.S. Application Ser. No. 62/120,091, filed Feb. 24, 2015, to which Applicant claims the benefit of the earlier filing date. This provisional application is incorporated herein by reference and made a part hereof.

BACKGROUND OF THE INVENTION

1. Field of the Invention

This invention relates to fixation systems, and more particularly, to a modular interspinous fixation system including a modular insert that can be mounted to or integral with a first plate and can be slidably received in a generally opposing second plate.

2. Description of the Related Art

Many types of devices for surgical stabilization of a spine have been developed. Various screw, rod and plating systems have been utilized for the purpose of stabilizing the spine for the purposes of fixation and spinal fusion. Until recently, such devices have been large constructs requiring extensive surgical exposure and operation time. There is an ongoing shift to provide spinal stabilization for fusing using more compact devices and devices that are simpler in operation. Furthermore, there is an increased need to be able to tailor these devices to the individual anatomy of a specific patient or the treatment needs of an individual diseased process.

More recently, devices which affix to the spinous processes of adjacent vertebrae have been developed, including U.S. Pat. Nos. 5,645,599; 5,836,948; 5,860,977; 6,048,342; 6,068,630; 6,440,169; 6,451,019; 6,478,796; 6,582,433; 6,641,585; 6,964,883; 6,695,842; 7,048,736; 7,201,751; 7,306,628; 7,585,316; and U.S. Patent Publication Nos. 2008/0177306 and 2008/0183211, all of which are incorporated herein by reference and made a part hereof. The prior art, however does not fully address the needs, so what is needed is a system and method that improves upon the prior art.

SUMMARY OF THE INVENTION

An object of one embodiment is to provide a modular interspinous fixation system and method that utilizes modular components.

Another object of one embodiment is to provide a modular interspinous fixation system and method that utilizes a modular insert that is removably mounted, permanently secured or integral with a plate member.

Still another object of one embodiment is to provide a modular insert and plate member that can be sized, shaped and adapted in response to a local anatomy or size of an interspinous space between, for example, a first spinous process and a second spinous process.

Still another object of one embodiment is to provide a system and method that is adapted to utilize a plurality of modular inserts to provide a user or surgeon with the opportunity to select a modular insert in response to a local anatomy prior to or at the time of surgery or even during surgery.

Still another object of one embodiment is to provide a plurality of modular inserts having different shapes, sizes, dimensions or configurations.

Yet another object of one embodiment is to provide a modular insert that allows the user or surgeon to select a desired modular insert at the time of surgery and place or mount the modular insert on a plate, such as a first plate and, thereafter, slidably insert at least a portion of the modular insert in and through a second plate.

Still another object of one embodiment is to provide a single coupling, connection or means for locking the first and second plates together and that utilizes the same means for moving the plates together into a compressive position.

Yet another object of one embodiment is to provide a modular insert that can be mounted onto a first plate and wherein the first plate receives and rotatably supports a screw.

Another object of one embodiment is to provide a plate and modular insert that once a screw is received therein, the modular insert is adapted, configured and sized to expose at least a portion of the screw thread so that it can mate with a mating screw thread, for example, on a second plate when the second plate is slidably received on the modular insert.

Still another object of one embodiment is to provide a system that substantially simultaneously locks the first and second plates together while also providing means to cause the first and second plates to be moved into compression with bone.

Another object of one embodiment is to provide a convenient kit having a plurality of modular inserts, second plate members and first plate members and screws.

In one aspect, one embodiment comprises an implant system comprising a first plate member, a second plate member, at least one modular insert having an opening adapted to receive a coupling member, thereby permitting the coupling member to be rotated or moved when the coupling member is received in the second plate member, and a coupling for coupling the first plate member to the second plate member and adapted to cause the first plate member and the second plate member to move towards each other and cooperate to compress bone in response to a predetermined actuation of the coupling.

In another aspect, another embodiment comprises a modular interspinous fixation system comprising a first member, a second member, one of the first member or the second member having at least one female thread associated therewith, the other of the first member or the second member supporting a generally elongated rotatable screw that mates with the at least one female thread, a modular insert extending between the end plates and generally enclosing the generally elongated rotatable screw, and at least a portion of the modular insert being slidable into and through one of the first member or the second member in response to rotation of the generally elongated rotatable screw.

In another aspect, another embodiment comprises an interspinous fixation system comprising a set of elongated end plates in parallel spaced opposing relation, the plates having opposing bone engaging projections, one of the end plates having spaced opposing threads disposed between spaced guide ways, the other end plate supporting an elongated rotatable screw extending between the opposing threads in the opposing end plate, a bone spacer module extending between the end plates and enclosing the screw, and the spacer module extending into the guide ways and slidable in the guide ways to maintain alignment of the end plates in response to rotation of the screw.

This invention, including all embodiments shown and described herein, could be used alone or together and/or in combination with one or more of the features covered by one or more of the following list of features:

The implant system wherein the coupling comprises a threaded member having at least a portion rotatably mounted in the first plate member.

The implant system wherein the a least a portion of the threaded member is comprises a head comprising a channel adapted to receive a lock to rotatably retain the at least a portion of the threaded member in the first plate member, thereby enabling the head to be rotatably docked in the first plate member.

The implant system wherein the lock is a set screw adapted to permit the threaded member to be rotatably retained in the first plate member when in a first or unlocked position and to engage the head to lock it against rotation when the set screw is set or tightened.

The implant system wherein at least one of the first plate member or the second plate member comprises at least one wall that defines a receiving channel having a first predetermined configuration, the at least one modular insert having at least one of a shape, size or configuration that generally complements a first predetermined shape to permit the at least one modular insert to be received in and translate or move in the receiving channel.

The implant system wherein the at least one coupling comprises at least one connecting member associated with at least one of the first plate member or the second plate member, at least one mating coupling associated with the other of the second plate member or the first plate member, respectively, adapted to receive the at least one connecting member to fix the first plate member to the second plate member.

The implant system wherein the at least one connecting member comprises at least one male threaded member and the at least one mating coupling comprises at least one female thread adapted to threadably receive the at least one male threaded member, the first plate member and the second plate member becoming closer together upon a rotation of the at least one male threaded member.

The implant system wherein the at least one male threaded member is rotatably mounted in the first plate member, the second plate member comprising a plate wall having the at least one female thread integrally or monolithically formed therein.

The implant system wherein the at least one female thread is interrupted.

The implant system wherein the at least one modular insert comprises at least one wall or projection, the second plate member comprising at least one guide slot adapted to receive the at least one wall or projection and permitting at least a portion of the at least one modular insert to pass through the at second plate member.

The implant system wherein the at least one female thread is interrupted and defines at least one female threaded aperture, the at least one guide slot being in communication with the at least one female threaded aperture.

The implant system wherein the at least one female threaded aperture and the at least one guide slot cooperate to define a modular insert receiving aperture configured and dimensioned to generally complement a configuration of the at least one modular insert so that the at least one modular insert can be received in the modular insert receiving aperture to permit at least a portion of the at least one modular insert to pass therethrough and through the second plate member.

The implant system wherein the at least one coupling comprises at least one male threaded member associated with the first plate member and at least one female threaded member associated with the second plate member, the at least one modular insert having at least one wall that defines a thread-exposing window in the at least one modular insert so that when the at least one connecting member is received in the at least one modular insert, at least a portion of at least one male threaded member is exposed for threadable engagement with the at least one female threaded member.

The implant system wherein the at least one coupling comprises at least one male threaded member associated with the first plate member and at least one female threaded member associated with the second plate member, the at least one modular insert having plurality of walls adapted to define a plurality of thread-exposing windows in the at least one modular insert so that when the at least one connecting member is received in the at least one modular insert, a plurality of portions of the at least one male threaded member are exposed for threadable engagement with the at least one female member.

The implant system wherein the at least one female threaded member comprises a first female thread portion and a second female thread portion integrally formed in the second plate member, the plurality of portions of the at least one female threaded member comprises a first exposed male threaded area and a second exposed male threaded area, the first and second exposed male threaded areas threadably engaging the first and second female thread portions, respectively, when the at least one modular insert is at least partially inserted into the second plate member.

The implant system wherein the at least one modular insert is adapted to be removebly secured, affixed or locked to at least one of the first plate member or the second plate member.

The implant system wherein the at least one modular insert is permanently secured to at least one of the first or second plate members.

The implant system wherein the implant system comprises at least one of a lock or locking members for removeably securing, affixing or locking the at least one modular insert to the at least one of the first plate member or the second plate member.

The implant system wherein the at least one of a lock or locking means comprises a male projection located on either the first plate member or the at least one modular insert and a female mating aperture located on the other of the first plate member or the at least one modular insert, the male projection and the female mating aperture being sized and dimension to permit a snap-fit or press fit, thereby securing, affixing or locking the at least one modular insert to the first plate member.

The implant system wherein the at least one of a lock or locking means comprises a plurality of male projection located on the first plate member and a female mating aperture located on the other of the first plate member or the at least one modular insert, the male projection and the female mating aperture being sized and dimension to permit a snap-fit or press fit, thereby securing, affixing or locking the at least one modular insert to the first plate member.

The implant system wherein the second plate member comprises a modular insert aperture for receiving the at least one modular insert and permitting the at least one modular insert to pass through the second plate member.

The implant system wherein the at least one modular insert and the receiving aperture are adapted to align the first plate member to the second plate member and provide a spacer therebetween.

The implant system wherein the coupling comprises a male threaded member associated with the first plate member, the at least one modular insert receiving the male threaded member, the at least one modular insert being configured to permit at least a portion of the male threaded member to threadably engage a mating female thread associated with the second plate member.

The implant system wherein the implant system comprises a plurality of modular inserts, at least some of the plurality of modular inserts being different shapes sizes or configurations.

The implant system wherein the implant system comprises a plurality of second plate members each having a modular receiving aperture adapted and configured to generally compliment a shape of at least one of the plurality of modular inserts, respectively.

The implant system wherein coupling comprises a male threaded member having a head, the first plate member having a set screw for engaging the threaded member and retaining it in the first plate member.

The implant system wherein head has a circumferential aperture for receiving the set screw in order to permit the male threaded member to rotate while being retained in the first plate member.

The implant system wherein at least a portion of the at least one modular insert comprises a predetermined shape that is generally I-shaped or generally H-shaped in cross section.

The implant system wherein the second plate member has an aperture that generally complements the predetermined shape so that the at least one modular insert can pass into and through the second plate member.

The implant system wherein each of the first plate member and the second plate member comprises at least one anti-movement feature.

The implant system wherein the first plate member comprises a first plate member surface and the second plate member comprises a second plate member surface, at least one anti-movement feature comprises a first plurality of pointed projections that extend from the first plate member surface and a second plurality of pointed projections that extend from the second plate member surface.

The modular interspinous fixation system wherein the first member rotatably supports the generally elongated rotatable screw, the second member comprising the at least one female thread having a first thread and a second thread that is spaced from and generally opposed to the first thread.

The modular interspinous fixation system wherein the second member comprises at least one guideway, the at least a portion of the modular insert being adapted and configured to be slidably received in the at least one guideway and facilitating maintaining alignment of the first and second members in response to or during rotation of the generally elongated rotatable screw.

The modular interspinous fixation system wherein the second member comprises a plurality of guide ways, the modular insert having a plurality of projections adapted and configured to be slidably received in the plurality of guide ways, respectively, to facilitate maintaining alignment of the first and second members in response to or during rotation of the generally elongated rotatable screw.

The modular interspinous fixation system wherein the first member rotatably supports the generally elongated rotatable screw, the second member comprising the at least one female thread having a first thread and a second thread that is spaced from and generally opposed to the first thread, the first thread and the second thread being disposed between at least two of the plurality of guide ways.

The modular interspinous fixation system wherein the first thread and the second thread defining a receiving area for receiving the generally elongated rotatable screw, the receiving area being in communication with at least one of the plurality of guide ways.

The modular interspinous fixation system wherein the receiving area is in communication with each of the plurality of guide ways.

The modular interspinous fixation system wherein the first member comprises a first member bone-engaging surface and the second member comprises a second member bone engaging surface, the modular interspinous fixation system having a plurality of bone-engaging projections located on at least one of the first member bone-engaging surface or the second member bone engaging surface.

The modular interspinous fixation system wherein generally elongated rotatable screw comprises a head that is received within a head-receiving aperture defined by a wall in the first member, the first member also comprising at least one anti-rotation lock for locking the head in an anti-rotation position.

The modular interspinous fixation system wherein the at least one anti-rotation lock is associated with the wall and comprises at least one of a flexible or resilient arm or a set screw associated with the head-receiving aperture.

The modular interspinous fixation system wherein the anti-rotation lock comprises the set screw, the head comprising a circumferential channel and set screw is adapted to be received in the circumferential channel and permit a threaded member to be rotatably retained in the first member when in a first or unlocked position and to engage the head to lock it against rotation when the set screw is set or tightened.

The modular interspinous fixation system wherein the modular insert comprises at least one wall that defines a thread-exposing window in the modular insert so that when the modular insert is received on the generally elongated rotatable screw, at least a portion of a thread is exposed for threadable engagement with the at least one female thread.

The modular interspinous fixation system wherein the modular insert comprises at least one wall that defines a thread-exposing window in the modular insert so that when the modular insert is received on the generally elongated rotatable screw, at least a portion of a thread is exposed for threadable engagement with the at least one female thread, the modular insert having plurality of walls adapted to define a plurality of thread-exposing windows in the modular insert so that when generally elongated rotatable screw is received in the modular insert, a plurality of portions of the a thread on the generally elongated rotatable screw are exposed for threadable engagement with the first thread and the second thread.

The modular interspinous fixation system wherein the second member comprises a first female thread portion and a second female thread portion integrally formed in the second member, the plurality of portions of the at least one female threaded member comprises a first exposed male threaded area and a second exposed male threaded area, the first and second exposed male threaded areas threadably engaging the first and second female thread portions, respectively, when the modular insert is at least partially inserted into the second member.

The modular interspinous fixation system wherein the modular insert is adapted to be removably secured, affixed or locked to at least one of the first member or the second member.

The modular interspinous fixation system wherein the modular insert is permanently secured to at least one of the first or second members.

The modular interspinous fixation system wherein the modular interspinous fixation system comprises at least one of a lock or locking members for removeably securing, affixing or locking the modular insert to the at least one of the first member or the second member.

The modular interspinous fixation system wherein the at least one of a lock or locking means comprises a male projection located on either the first member or the modular insert and a female mating aperture located on the other of the first member or the modular insert, the male projection and the female mating aperture being sized and dimension to permit a snap-fit or press fit, thereby securing, affixing or locking the modular insert to the first member.

The modular interspinous fixation system wherein the at least one of a lock or locking means comprises a plurality of male projection located on the first member and a female mating aperture located on the other of the first member or the modular insert, the male projection and the female mating aperture being sized and dimension to permit a snap-fit or press fit, thereby securing, affixing or locking the modular insert to the first member.

The modular interspinous fixation system wherein the second member comprises a modular insert aperture for receiving the modular insert and permitting the modular insert to pass through the second member.

The modular interspinous fixation system wherein the modular insert and the receiving aperture are adapted to align the first member to the second member and provide a spacer therebetween.

The modular interspinous fixation system wherein the modular interspinous fixation system comprises a plurality of modular inserts, at least some of the plurality of modular inserts being different shapes sizes or configurations.

The modular interspinous fixation system wherein the modular interspinous fixation system comprises a plurality of second members each having a modular insert receiving aperture adapted and configured to generally compliment a shape of at least one of the plurality of modular inserts, respectively.

The modular interspinous fixation system wherein the second member has a modular insert aperture that generally complements a predetermined shape so that the modular insert can pass into and through the second member.

The modular interspinous fixation system wherein at least a portion of the modular insert comprises a predetermined shape that is generally I-shaped or generally H-shaped in cross section.

The modular interspinous fixation system wherein the second member comprises a plurality of guide ways that cooperate with a screw-receiving aperture to define the modular insert aperture.

These and other objects and advantages of the invention will be apparent from the following description, the accompanying drawings and the appended claims.

BRIEF DESCRIPTION OF THE ACCOMPANYING DRAWINGS

FIG. 1 is a perspective view of a first plate, having a modular insert attached thereto and generally enclosing an elongated rotatable screw;

FIG. 2 is an exploded view of a modular interspinous fixation system and threaded component;

FIG. 3A is another exploded view showing other details of the embodiment shown in FIG. 2;

FIG. 3B is another perspective exploded view showing further details of the embodiment shown in FIG. 2;

FIG. 6A is a perspective view of the modular insert shown in FIG. 1;

FIG. 6B is another view of the modular insert shown in FIG. 6A showing features of a nose of the modular insert;

FIG. 6C is a sectional view taken along the line 6C-6C in FIG. 6A;

FIG. 6D is a sectional view taken along the line 6D-6D in FIG. 6B;

FIG. 7 is various views of different modular inserts and second plates showing different shapes, sizes and/or configurations that may be used in the system.

DETAILED DESCRIPTION OF THE PREFERRED EMBODIMENTS

Figure 4:
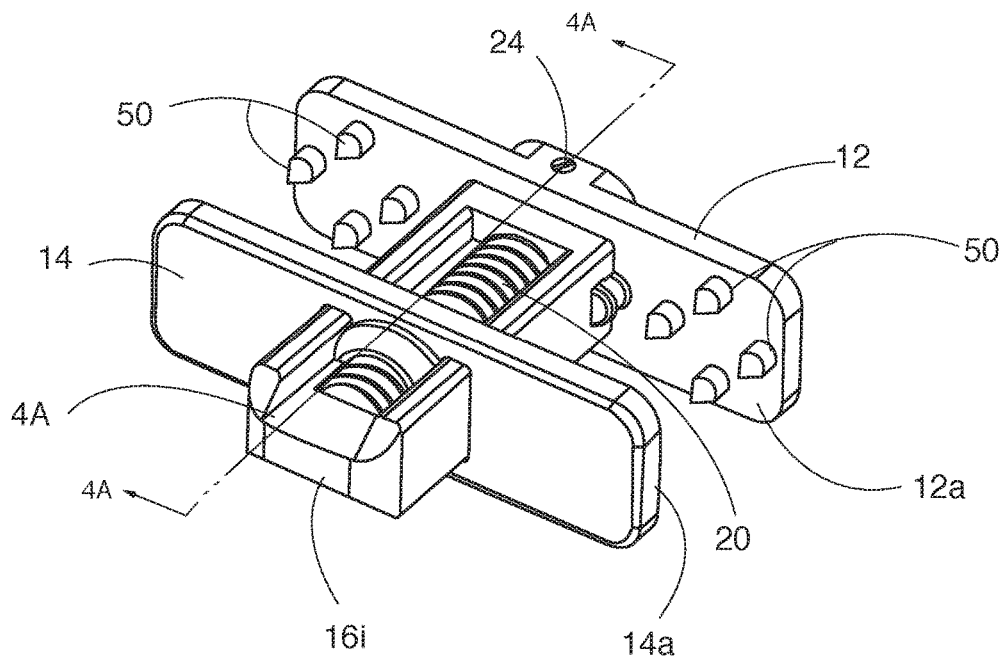
FIG. 4 is a view illustrating the modular insert passing through a second plate and after the elongated rotatable screw has been screwed.

Referring now to FIG. 1, a modular interspinous fixation system or implant system 10 is shown. The modular interspinous fixation system or implant system 10 comprises a first member or first plate member 12 and a second member or second plate member 14.

The modular interspinous fixation system or implant system 10 comprises at least one or a plurality of modular inserts 16 having a first end 17a and a second end 17b. As will be described later herein, the first end 16a is detachably secured to a wall 12a of the first plate member 12. As best illustrated in FIG. 2, the modular interspinous fixation system or implant system 10 comprises a coupling or connector 18 for detachably coupling the first plate member 12 to the second plate member 14. In the illustration being described, the coupling or connector 18 is adapted to cause the first plate member 12 and the second plate member 14 to move towards or away from each other, and into compression with bone in response to a predetermined actuation of the coupling or connector 18. In the illustration being described, the coupling or connector 18 comprises a threaded member or screw 20 that is rotatable and elongated and that has a head 22 that is rotatably received in an aperture 33 (FIG. 1) defined by a stepped wall 52 in order to retain the head 22 in the first plate member 12 using a set screw 24 as illustrated.

Figure 4A:
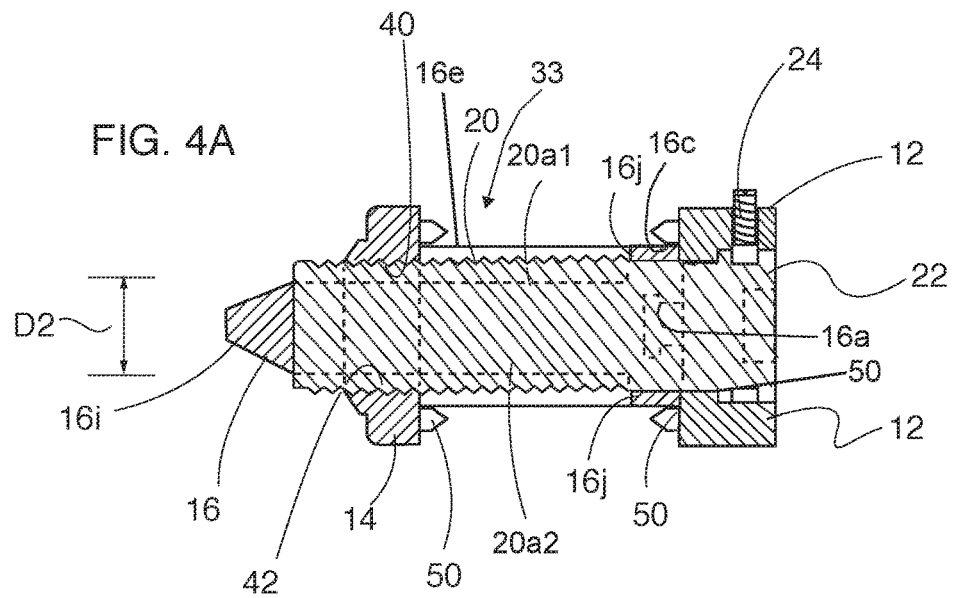
FIG. 4A is a sectional view taken along the line 4A-4A in FIG. 4.

As best illustrated in FIGS. 2 and 4A, note that the head 22 comprises a generally U-shaped wall 22a that defines a circumferential channel 26 as shown. As best illustrated in FIG. 4A, the channel 26 of the head 22 receives the set screw 24. In the illustration being described, when the set screw 24 is slightly untightened, the screw 20 can be rotated or screwed using a tool (not shown) that is inserted into the hex opening 28. As described later herein, after the screw 20 is rotated, the set screw 24 can be tightened to lock the screw 20. Although not shown, other types of screw head locks may be utilized, such as the locking system shown in U.S. Pat. Nos. 7,182,782; 7,655,028; 7,641,701; 8,821,553; 8,372,152; 8,062,367; 8,282,682; 8,734,493; 8,795,370 and U.S. Patent Publications No. 2014/0324173; all of which are incorporated herein by reference and made a part hereof.

Referring now to FIGS. 2 and 4A, note that the first plate member 12 has a wall 53 having a seat or shoulder 55 that becomes generally opposed to a surface 22a1 of the screw head 22 to support the screw head 22 in the head receiving area 52 after the screw head 22 has been received in the head receiving area 52 of the first plate member 12, the set screw 24 may be screwed into the thread 25 (FIG. 2) in order to lock the screw 20 in the first plate member 12.

Figure 8:
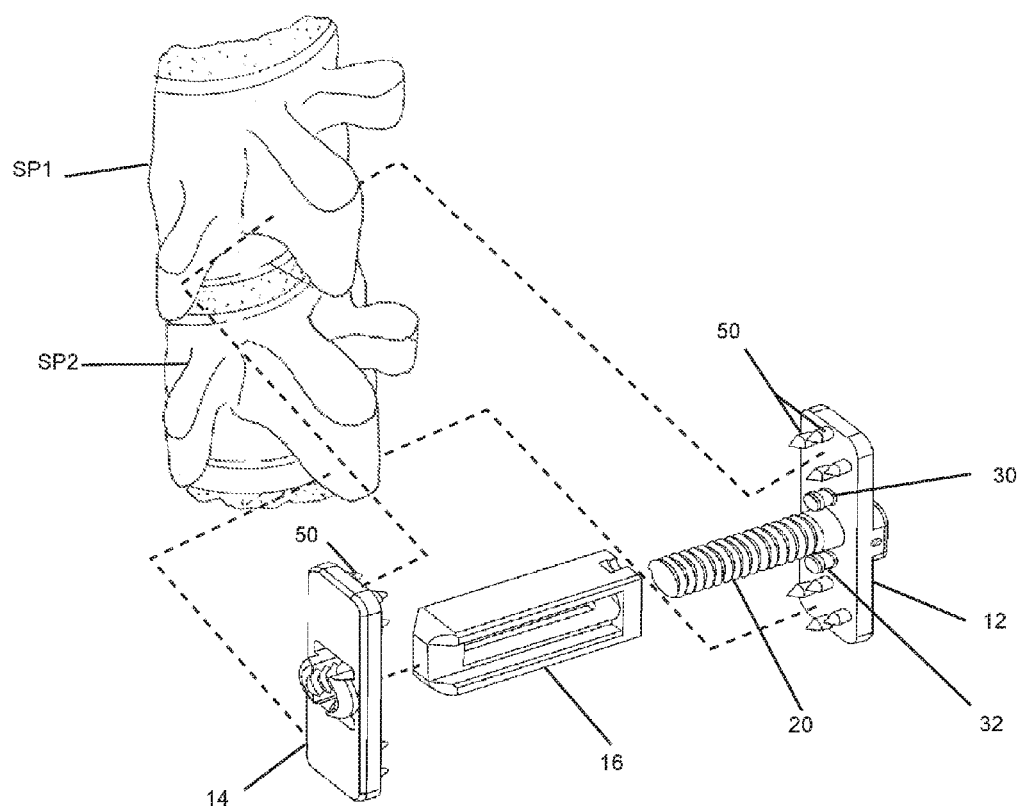
FIG. 8 is an exploded view of the modular interspinous fixation system and threaded component.

Note that the modular insert 16 is detachably locked or mounted onto the wall 12a of the first plate member 12. In this regard, the modular insert 16 comprises two semi-circular and stepped walls 16a and 16b that define two laterally extending channels 16a1 and 16b1. The laterally extending channels 16a1 and 16b1 are adapted to receive a first male locking projection 30 and a second male locking projection 32, respectively. In the illustration being described, the first male locking projection 30 and the second male locking projection 32 are somewhat elastic and flexible and are also stepped and complement the shape of the laterally extending channels 16a1 and 16b1, respectively, so that the modular insert 16 can be detachably snap-fit onto the first male locking projection 30 and the second male locking projection 32 in order to detachably secure the modular insert 16 to the first plate member 12. It should be understood that in the illustration being described, the modular interspinous fixation system or implant system 10 is adapted and provided with a plurality of modular inserts of different sizes, shapes or configurations, such as the modular inserts 16-16''' in FIG. 7. In the illustration being described, the surgeon selects the modular insert 16 based upon the anatomical environment of the patient. In this regard, the modular insert 16 may act as a support or spacer that is situated between two bones, such as a first spinous process SP1 (FIG. 8) and a second spinous process SP2 (FIG. 8).

Once a surgeon has selected the modular insert 16, it may be provided on the first plate member 12 or detachably secured to the first plate member 12 by snap-fitting the first male locking projection 30 (FIG. 3B) and the second male locking projection 32 into the laterally extending channels 16a1 and 16b1, respectively, thereby locking the modular insert 16 onto the first plate member 12. The modular insert 16 is adapted to receive and generally or partially encloses the threaded portion 20a of the screw 20 after the screw 20 is rotatably mounted into the first plate member 12. In this regard, note that the modular insert 16 comprises a generally circular wall 16c (FIGS. 2, 3A, 3B, 6A and 6B) that defines a screw-receiving aperture or opening 16d. Note that when the modular insert 16 is mounted on the first plate member 12, the screw 20 and threaded portion 20a are received in the aperture 16d as shown.

Figure 5A:
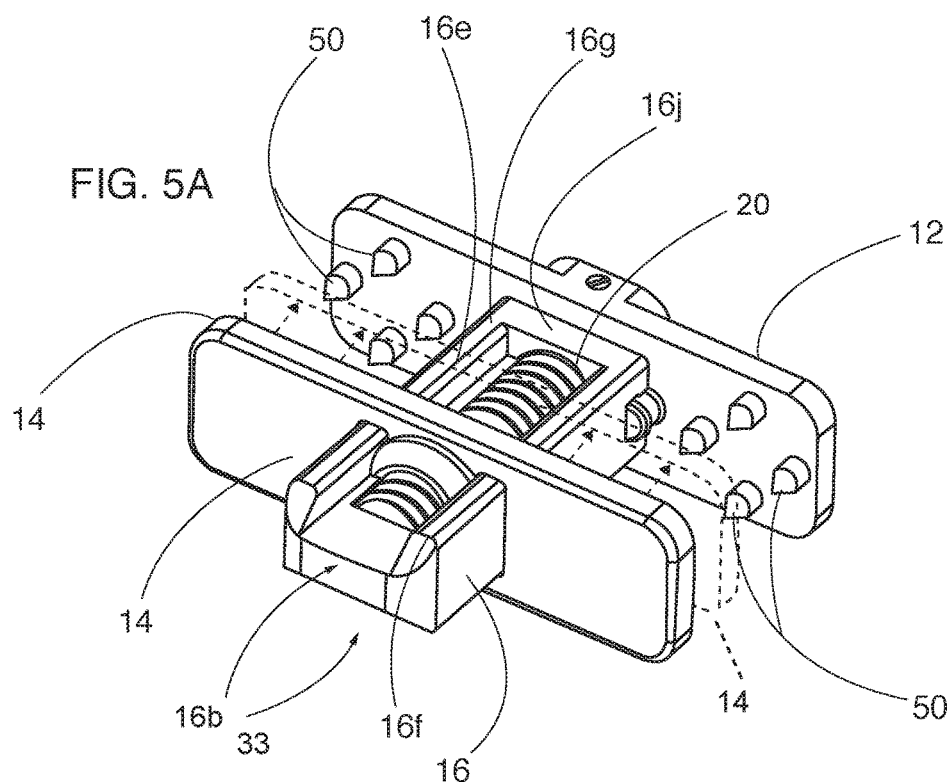
FIG. 5A is a view similar to FIG. 4 but showing the plates in a different position relative to each other and in response to rotation of the screw.
Figure 5B:
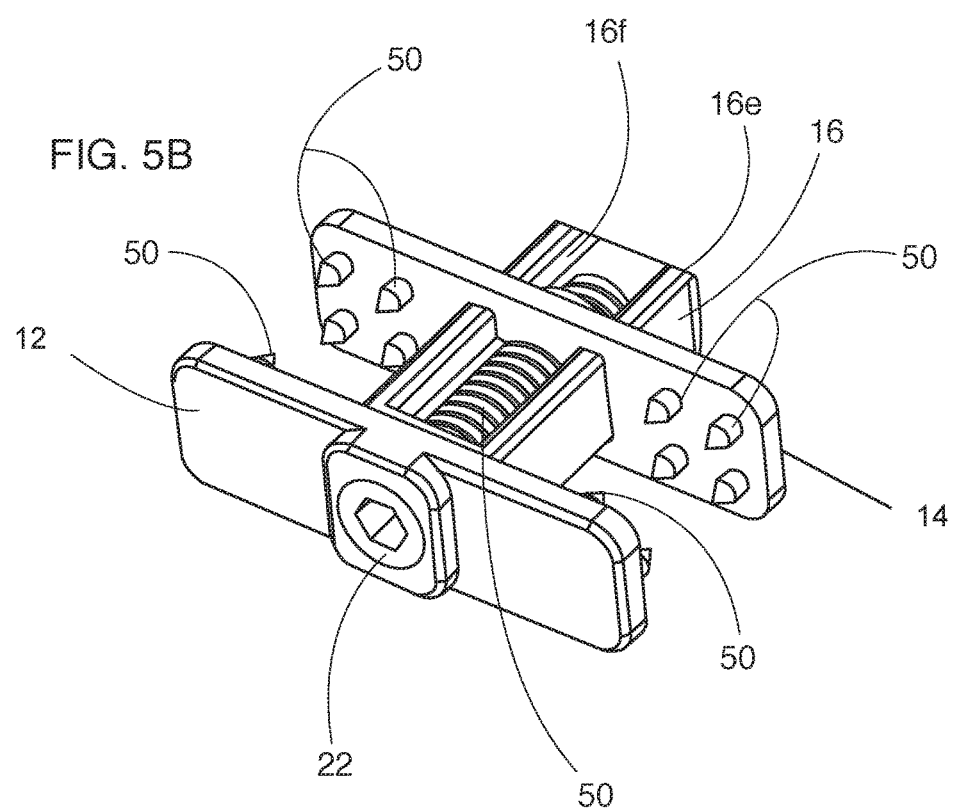
FIG. 5B is a bottom perspective view of the embodiment shown in FIG. 4.

Note in FIGS. 5A-5B and 6C, that the modular insert 16 comprises a first wall 16e and a generally opposed second wall 16f. The first wall 16e comprises a first wall portion 16e1, a second wall portion 16e2 and a third wall portion 16e3. Likewise, the second wall 16f, comprises a first wall portion 16f1, a second wall portion 16f2 and a third wall portion 16f3. In the illustration being described, the first wall portion 16e1 generally opposes and cooperates with the first wall portion 16f1 to define a first opening or window 33 (FIG. 4A). Likewise, the wall portions 16e3 and 16f3 are generally opposed and cooperate to define a second opening or window 35 as shown. The wall portion 16e2 generally opposes the wall portion 16f2 and they are arcuate or curved as shown and generally complement a shape of the screw 20 and cooperate to rotatably support the screw 20. It is important to note as best illustrated in FIGS. 1, 4, 4A and 5A-5B that the wall portions 16e2 and 16f2 are dimensioned such that the dimension D1 (FIGS. 4A and 6C) is slightly smaller than a diameter of the threaded portion 20a of the screw 20, which are adapted to permit a first portion 20a1 and a second portion 20a2 of the threaded portion 20a to be exposed. In this regard, note that the second plate member 14 comprises a first female thread 40 and a generally opposing second female thread 42 as illustrated in FIGS. 2 and 4A. Advantageously, having the first portion 20a1 and the second portion 20a2 of the threaded portion 20a exposed permits them to threadably engage with the first female thread 40 and the second female thread 42 when the modular insert 16 is inserted into a modular insert opening or receiving area 44 (FIG. 2) in the second plate member 14. In this regard, note that a nose 16i of the modular insert 16 generally opposes a rear wall 16j at end 16a. As mentioned earlier herein, the rear wall 16j comprises the circular wall 16c that defines the generally circular opening 16d. Note that a dimension D2 (FIG. 4A) of the nose 16i is also smaller than the diameter of the threaded portion 20a. The nose 16i has beveled surfaces adapted to facilitate guiding and inserting the modular insert 16 into the modular insert aperture 44.

Referring back to FIGS. 1, 2 and 4A-5B, note that the modular insert 16 extends between the first plate member 12 and the second plate member 14 and through the second plate member 14 as illustrated in FIG. 4. Notice how the modular insert 16 captures and generally encloses the screw 20 and threaded portion 20a as illustrated in FIG. 1. At least a portion of the modular insert 16 is slidable into and through the second plate member 14 particularly in response to a rotation of the generally elongated screw 20. Notice that the second plate member 14 comprises at least one female screw thread 40. In the illustration being described, the second plate member 14 comprises the first female screw thread 40 and the second female screw thread 42 that generally opposes the first female screw thread 40 as shown. In the illustration being described, the second plate member 14 also comprises at least one or a plurality of guide ways. In this regard, notice that the second plate member 14 comprises a first guide way wall 46 and a second guide way wall 48 that define a first guide way 46a and a second guide way 48a, respectively. In one illustrative embodiment, the first and second threads 40 and 42 cooperate to define the receiving area 44 for receiving the threaded portion 20a of the screw 20. Note that the receiving area 44 is in communication with at least one of the guide ways 46a and 48a as shown. In one illustrative embodiment, the receiving area 44 is in communication with both guide ways 46a and 48a.

As illustrated in FIG. 6C, the modular insert 16 has a generally I or H shape in cross section. In the illustration being described, the shape, size, dimension and configuration of the modular insert 16 is such that it generally complements a shape of the guide ways 46a and 48a and the receiving area 44. In the illustration being described, the complementary shape of the modular insert 16 and the guide ways 46a and 48a and the receiving area 44 are configured such that the modular insert 16 can be slidably guided and received in the second plate member 14. This feature facilitates maintaining alignment of the first and second plate member 12 and 14 in response to or during rotation of the generally elongated screw 20. When the screw 20 is inserted into the first plate member 12 and into the modular insert 16, the portions 20a1 and 20a2 may threadably engage with the first female thread 40 and second female thread 42, respectively, as shown. The screw 20 may then be rotated which causes the second plate member 14 to move toward the first plate member 12 as illustrated in FIGS. 4, 5A and 6. The screw 20 may be rotated using the tool (not shown) to apply a compressive force in order to secure the first and second plate members 12 and 14 and the modular insert 16 into compressive engagement with the bone of a patient. It should be appreciated that one significant advantage of this design is that the coupling or connector 18 of the screw 20 cooperates with the first and second female threads 40 and 42 and not only function to couple the first and second plate members 12 and 14 together, but also causes the first and second plate members 12 and 14 to apply a compressive force against the bone(s) of the patient as illustrated in FIG. 4.

Each of the first and second plate members 12 and 14 may comprise at least one or a plurality of anti-movement features or means. The at least one or plurality of anti-movement features comprises a plurality of anti-movement projections 50 as shown. When the first and second plate members 12 and 14 are mounted on the patient, the plurality of anti-movement projections 50 engage bone and facilitate preventing the first and second plate members 12 and 14 from moving after they are mounted in place.

During a surgical procedure and after the surgeon has selected the appropriate sized modular insert 16-16''' (FIG. 7), the set screw 24 may be loosened to permit the screw 20 to be received in the first plate member 12 and even after having been received in the first plate member 12. The modular insert 16 may be mounted onto the first plate member 12 either prior to mounting the screw 20 in the first plate member 12 or after the screw 20 has been received in the first plate member 12. After the first plate member 12, the modular insert 16 and the screw 20 are assembled as illustrated in FIG. 1, then the second plate member 14 can be selected and then slidably mounted or positioned on the modular insert 16 as mentioned and shown. Note again, that this may be performed either prior to or during the surgical procedure. After the first plate member 12 and second plate member 14 are compressed against bone, the surgeon may set the set screw 24 in order to lock the screw 20 in the first plate member 12. Although not shown, other means may be provided on, integral or monolithically formed with the first plate member 12 in order to lock the screw 20 in place. For example, some of the features of the aforementioned U.S. patents may be provided with the first plate member 12 in order to lock the screw 20 in the first plate member 12.

As illustrated in FIG. 7, it should be emphasized that the modular interspinous fixation system or implant system 10 is a modular system and is intended to be used with modular inserts 16 of different shapes, sizes or configurations, all of which may be provided in a single kit to enable a surgeon to select the appropriate modular insert 16 for use during a particular procedure. FIG. 7 illustrates four illustrative examples of the modular inserts 16, 16', 16" and 16''' of different shapes, sizes and/or configurations. Advantageously, this allows for a selection of modular inserts 16-16''' to conform to the patient's interspinous space.

ADDITIONAL CONSIDERATIONS

Advantageously, the locking means or lock in the form of the first and second male projections 30 and 32 that cooperate with the walls 16a and 16b enable the modular insert 16 to be locked onto the first plate member 12 in a manner that prevents release or rotation of the modular insert 16. The guide ways 46a and 48a of the second plate member 14 also facilitate preventing rotation of the modular insert 16 and also maintain alignment of the first and second plate members 12 and 14 as they move together in response to rotation of the screw 20.

Although not shown, the coupling or connector 18 between the first and second plate members 12 and 14 has been shown and described as the screw 20 cooperating with the first and second female threads 40 and 42, it should be understood that other types of non-threaded connection or connectors could be used.

In the illustration being described, the second plate member 14 has been shown and described with a plurality of opposing female threads 40 and 42. These could be viewed as a single, but interrupted, female thread.

Note that the various surfaces of the modular insert 16, such as the nose 16i and walls 16e1, 16e3, 16f1 and 16f3, may have surfaces that are beveled or even rounded to facilitate guiding and inserting the modular insert 16 or at least a portion thereof into and through the second plate member 14.

This invention, including all embodiments shown and described herein, could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A modular interspinous fixation system comprising:
   a first member;
   a second member;
   one of said first member or said second member having at least one female thread associated therewith;
   the other of said first member or said second member supporting a generally elongated rotatable screw that mates with said at least one female thread;
   a modular insert extending between the end plates and generally enclosing said generally elongated rotatable screw; and
   at least a portion of said modular insert being slidable into and through one of said first member or said second member in response to rotation of said generally elongated rotatable screw
   wherein said second member comprises a plurality of guide ways, said modular insert having a plurality of projections adapted and configured to be slidably received in said plurality of guide ways, respectively, to facilitate maintaining alignment of said first and second members in response to or during rotation of said generally elongated rotatable screw, wherein said first member rotatably supports said generally elongated rotatable screw, said second member comprising said at least one female thread having a first thread and a second thread that is spaced from and generally opposed to said first thread, said first thread and said second thread being disposed between at least two of said plurality of guide ways, wherein said first thread and said second thread defining a receiving area for receiving said generally elongated rotatable screw;

said receiving area being in communication with at least one of said plurality of guide ways, wherein said receiving area is in communication with each of said plurality of guide ways.

2. The modular interspinous fixation system as recited in claim 1, wherein said first member comprises a first member bone-engaging surface and said second member comprises a second member bone engaging surface, said modular interspinous fixation system having a plurality of bone-engaging projections located on at least one of said first member bone-engaging surface or said second member bone engaging surface.

3. The modular interspinous fixation system as recited in claim 1 wherein generally elongated rotatable screw comprises a head that is received within a head-receiving aperture defined by a wall in said first member, said first member also comprising at least one anti-rotation lock for locking said head in an anti-rotation position.

4. The modular interspinous fixation system as recited in claim 3 wherein said at least one anti-rotation lock is associated with said wall and comprises at least one of a flexible or resilient arm or a set screw associated with said head-receiving aperture.

5. The modular interspinous fixation system as recited in claim 4 wherein said anti-rotation lock comprises said set screw, said head comprising a circumferential channel and set screw is adapted to be received in said circumferential channel and permit a threaded member to be rotatably retained in said first member when in a first or unlocked position and to engage said head to lock it against rotation when the set screw is set or tightened.

6. The modular interspinous fixation system as recited in claim 1 wherein said modular insert comprises at least one wall that defines a thread-exposing window in said modular insert so that when said modular insert is received on said generally elongated rotatable screw, at least a portion of a thread is exposed for threadable engagement with said at least one female thread.

7. The modular interspinous fixation system as recited in claim 1, wherein said modular insert comprises at least one wall that defines a thread-exposing window in said modular insert so that when said modular insert is received on said generally elongated rotatable screw, at least a portion of a thread is exposed for threadable engagement with said at least one female thread;
said modular insert having plurality of walls adapted to define a plurality of thread-exposing windows in said modular insert so that when generally elongated rotatable screw is received in said modular insert, a plurality of portions of said a thread on said generally elongated rotatable screw are exposed for threadable engagement with said first thread and said second thread.

8. The modular interspinous fixation system as recited in claim 7 wherein said second member comprises a first female thread portion and a second female thread portion integrally formed in said second member, said plurality of portions of said at least one female threaded member comprises a first exposed male threaded area and a second exposed male threaded area;
said first and second exposed male threaded areas threadably engaging said first and second female thread portions, respectively, when said modular insert is at least partially inserted into said second member.

9. The modular interspinous fixation system as recited in claim 1 wherein said modular insert is adapted to be removably secured, affixed or locked to at least one of said first member or said second member.

10. The modular interspinous fixation system as recited in claim 1 wherein said modular insert is permanently secured to at least one of said first or second members.

11. The modular interspinous fixation system as recited in claim 9 wherein said modular interspinous fixation system comprises at least one of a lock or locking members for removeably securing, affixing or locking said modular insert to said at least one of said first member or said second member.

12. The modular interspinous fixation system as recited in claim 11 wherein said at least one of a lock or locking means comprises a male projection located on either said first member or said modular insert and a female mating aperture located on the other of said first member or said modular insert, said male projection and said female mating aperture being sized and dimension to permit a snap-fit or press fit, thereby securing, affixing or locking said modular insert to said first member.

13. The modular interspinous fixation system as recited in claim 12 wherein said at least one of a lock or locking means comprises a plurality of male projection located on said first member and a female mating aperture located on the other of said first member or said modular insert, said male projection and said female mating aperture being sized and dimension to permit a snap-fit or press fit, thereby securing, affixing or locking said modular insert to said first member.

14. The modular interspinous fixation system as recited in claim 1 wherein said second member comprises a modular insert aperture for receiving said modular insert and permitting said modular insert to pass through said second member.

15. The modular interspinous fixation system as recited in claim 14 wherein said modular insert and said receiving aperture are adapted to align said first member to said second member and provide a spacer therebetween.

16. The modular interspinous fixation system as recited in claim 1 wherein said modular interspinous fixation system comprises a plurality of modular inserts, at least some of said plurality of modular inserts being different shapes sizes or configurations.

17. The modular interspinous fixation system as recited in claim 16 wherein said modular interspinous fixation system comprises a plurality of second members each having a modular insert receiving aperture adapted and configured to generally compliment a shape of at least one of said plurality of modular inserts, respectively.

18. The modular interspinous fixation system as recited in claim 1 wherein said second member has a modular insert aperture that generally complements a predetermined shape so that said modular insert can pass into and through said second member.

19. The modular interspinous fixation system as recited in claim 1 wherein at least a portion of said modular insert comprises a predetermined shape that is generally I-shaped or generally H-shaped in cross section.

20. The modular interspinous fixation system as recited in claim 18 wherein said second member comprises a plurality of guide ways that cooperate with a screw-receiving aperture to define said modular insert aperture.

* * * * *